United States Patent
Mason

(10) Patent No.: US 7,163,560 B2
(45) Date of Patent: Jan. 16, 2007

(54) METHOD FOR GRAFTLESS SPINAL FUSION

(76) Inventor: Michael D. Mason, 235 Cypress St., Suite 200, Brookline, MA (US) 02445

( * ) Notice: Subject to any disclaimer, the term of this patent is extended or adjusted under 35 U.S.C. 154(b) by 0 days.

(21) Appl. No.: 10/767,637

(22) Filed: Jan. 29, 2004

(65) Prior Publication Data

US 2004/0186578 A1    Sep. 23, 2004

Related U.S. Application Data

(62) Division of application No. 09/976,685, filed on Oct. 11, 2001, now Pat. No. 6,743,256.

(60) Provisional application No. 60/239,368, filed on Oct. 11, 2000.

(51) Int. Cl.
 *A61F 2/44* (2006.01)
(52) U.S. Cl. .................................. 623/17.16
(58) Field of Classification Search .. 623/17.11–17.16, 623/23.5, 23.62, 23.63; 128/892
See application file for complete search history.

(56) References Cited

U.S. PATENT DOCUMENTS

| | | | | |
|---|---|---|---|---|
| 4,714,469 | A | * 12/1987 | Kenna | .......................... 606/61 |
| 4,828,563 | A | * 5/1989 | Muller-Lierheim | ...... 623/23.63 |
| 4,904,261 | A | 2/1990 | Dove et al. | |
| 4,946,378 | A | * 8/1990 | Hirayama et al. | ........ 623/17.16 |
| 5,071,437 | A | * 12/1991 | Steffee, Arthur D. | .... 623/17.16 |
| 5,112,354 | A | 5/1992 | Sires | .............................. 623/16 |
| 5,314,477 | A | * 5/1994 | Marnay | ..................... 623/17.15 |
| 5,344,654 | A | 9/1994 | Rueger et al. | .............. 424/423 |
| 5,571,109 | A | 11/1996 | Bertagnoli | |
| 5,609,635 | A | 3/1997 | Michelson | .................... 623/17 |
| 5,645,591 | A | 7/1997 | Kuberasampath et al. | .... 623/16 |
| 5,709,683 | A | 1/1998 | Bagby | |
| 5,824,094 | A | * 10/1998 | Serhan et al. | ............ 623/17.16 |
| 5,865,848 | A | 2/1999 | Baker | ........................... 623/17 |
| 5,888,222 | A | 3/1999 | Coates et al. | ................. 623/17 |
| 5,888,223 | A | * 3/1999 | Bray, Jr. | ................... 623/17.16 |
| 5,888,227 | A | * 3/1999 | Cottle | ..................... 623/17.16 |
| 5,984,967 | A | 11/1999 | Zdeblick et al. | .............. 623/17 |

(Continued)

FOREIGN PATENT DOCUMENTS

DE    39 11 610 A    10/1990

(Continued)

OTHER PUBLICATIONS

International Search Report, International Application No. PCT/US 01/31821, Mailed May 17, 2002.

*Primary Examiner*—Eduardo C. Robert
*Assistant Examiner*—Annette R. Reimers
(74) *Attorney, Agent, or Firm*—Bromberg & Sunstein LLP

(57) ABSTRACT

A graftless spinal implant for mechanically attaching two adjacent vertebrae includes a body having first and second opposite surfaces. The first and second surfaces include at least one protruding member for securing the body to adjacent vertebrae, wherein the exterior surfaces of the body and the first and second protruding members include a bioactive coating. The bioactive coating can be selected from coatings such as for example, hydroxyapatite. The exterior bioactive coating facilitates the ongrowth/ingrowth of vertebral bone between the implantable spinal fusion device and adjacent vertebrae. Advantageously, spinal fusion may be achieved without the use of a bone graft and/or bone growth agents.

2 Claims, 7 Drawing Sheets

U.S. PATENT DOCUMENTS

| | | | |
|---|---|---|---|
| 6,039,762 A | 3/2000 | McKay | 623/17 |
| 6,096,080 A | 8/2000 | Nicholson | 623/17 |
| 6,113,638 A | 9/2000 | Williams et al. | 623/17 |
| 6,210,412 B1 | 4/2001 | Michelson | 606/61 |
| 6,241,733 B1 | 6/2001 | Nicholson et al. | 606/84 |
| 6,241,769 B1 * | 6/2001 | Nicholson et al. | 623/17.11 |
| 6,241,770 B1 | 6/2001 | Michelson | |
| 6,241,771 B1 | 6/2001 | Gresser et al. | 623/17.16 |
| 6,261,586 B1 | 7/2001 | McKay | 424/423 |
| 6,264,656 B1 | 7/2001 | Michelson | 606/61 |
| 6,294,187 B1 | 9/2001 | Boyce et al. | 424/422 |
| 6,296,667 B1 | 10/2001 | Johnson et al. | 623/23.61 |
| 6,419,704 B1 | 7/2002 | Ferree | |
| 6,592,624 B1 * | 7/2003 | Fraser et al. | 623/17.16 |

FOREIGN PATENT DOCUMENTS

| | | | |
|---|---|---|---|
| EP | 0 317 972 | 5/1989 | |
| EP | 0-317-972 | 5/1989 | |
| EP | 0-421-485 | 4/1991 | |
| EP | 0 421 485 A | 4/1991 | |
| EP | 0421485 * | 4/1991 | 623/17.16 |
| WO | WO 90/00037 | 1/1990 | |
| WO | WO 90/11740 | 10/1990 | |
| WO | WO 93/22990 | 5/1993 | |
| WO | WO 93 22990 A | 11/1993 | |
| WO | WO 99/22675 | 5/1999 | |
| WO | WO 00/42954 | 7/2000 | |

* cited by examiner

METHOD FOR GRAFTLESS SPINAL FUSION

This application is a divisional application of U.S. patent application Ser. No. 09/976,685, entitled "Graftless Spinal Fusion Device," filed Oct. 11, 2001 now U.S. Pat. No. 6,743,256, which claims priority from the provisional application designated Ser. No. 60/239,368, filed Oct. 11, 2000 entitled "Spinal Fusion Device." Each of these applications is hereby incorporated by reference herein.

BACKGROUND OF THE INVENTION

The present invention relates to spinal implants, and in particular to a graftless spinal implant that employs a bioactive coating such as hydroxyapatite to promote fixation of the implant to adjacent bony surfaces.

U.S. Pat. No. 6,241,769 entitled "Implant for Spinal Fusion" and U.S. Pat. No. 6,096,080 entitled "Apparatus for Spinal Fusion Using Implanted Devices" disclose spinal replacement devices. Both patents discuss in detail the problems associated with the prior art devices.

The devices disclosed in U.S. Pat. Nos. 6,241,769 and 6,096,080, each hereby incorporated by reference, utilize a central graft space for promoting the long-term fixation onto adjacent bony surfaces. The device can be fabricated from human bone allograft material of bone substitute material such as coral or calcium phosphate. A problem with the devices disclosed in these patents is that they require a bone graft, and the failure rate of these types of devices is fairly high. In addition, there is an unacceptably high rate of morbidity (e.g., 30%).

Therefore, there is a need for a spinal implant device that does not utilize a bone graft in an attempt to facilitate fixation of the implant device to adjacent vertebral bony surfaces, and thereby stabilize the spinal motion segment.

SUMMARY OF THE INVENTION

Briefly, according to the present invention, an implantable spinal fusion device includes an exterior bioactive coating.

In one embodiment, a graftless spinal implant for mechanically attaching two adjacent vertebrae includes a body having first and second opposite surfaces. The first and second surfaces include at least one protruding member for securing the body to adjacent vertebrae, wherein the exterior surfaces of the body and the first and second protruding members include a bioactive coating.

The bioactive coating can be selected from coatings such as for example, hydroxyapatite, bioglass, biocomposites, hydroxypatite tricalcium phosphate, bone morphogenic protein, or other bone producing proteins.

The exterior bioactive coating facilitates the ongrowth/ingrowth of vertebral bone between the implantable spinal fusion device and adjacent vertebrae. Advantageously, this allows the device to avoid the use of a bone graft and/or bone growth agents.

These and other objects, features and advantages of the present invention will become apparent in light of the following detailed description of preferred embodiments thereof, as illustrated in the accompanying drawings.

DETAILED DESCRIPTION OF THE INVENTION

Figure 1:
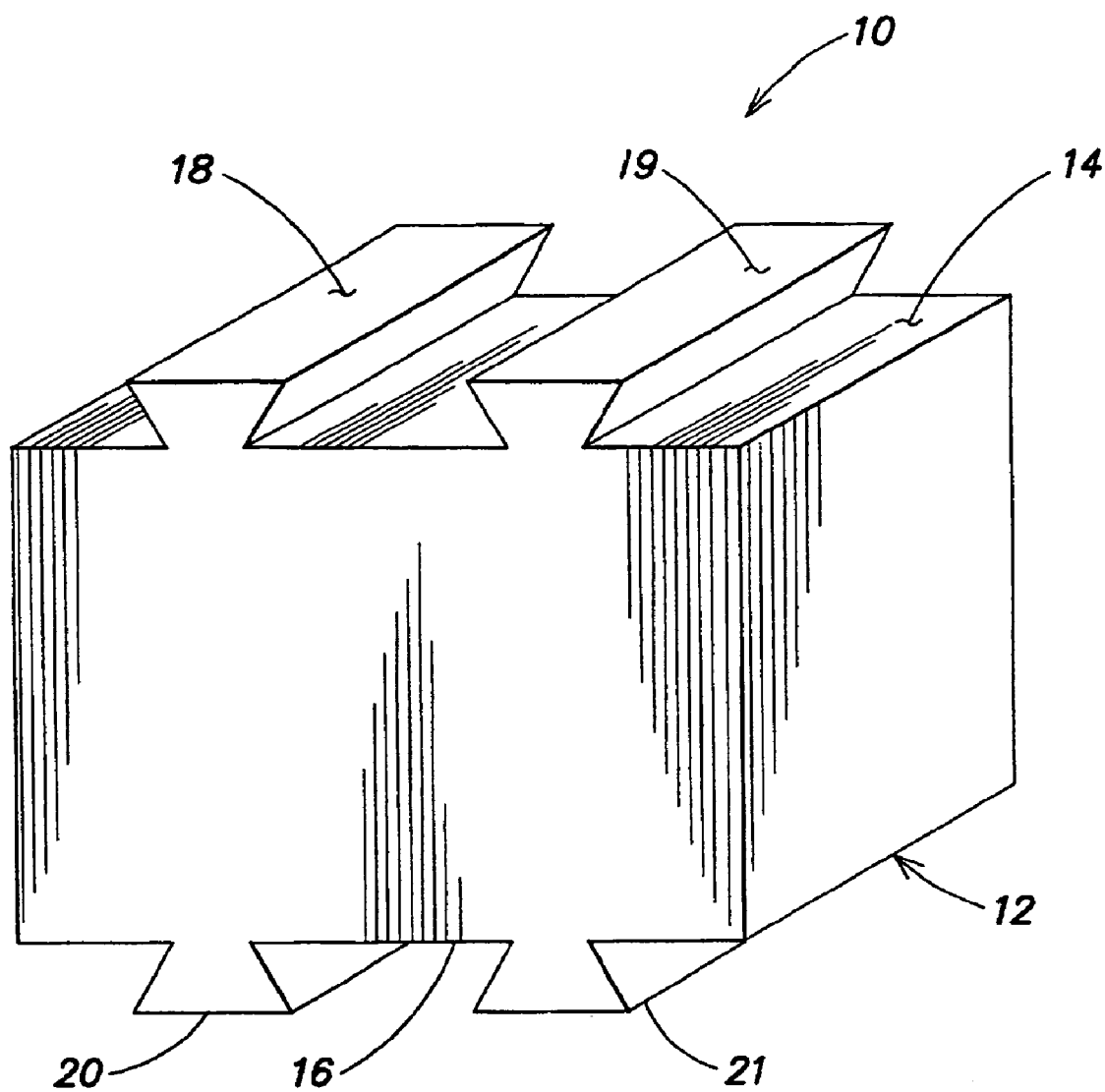
FIG. 1 illustrates a perspective view of a first embodiment of a graftless spinal implant.

FIG. 1 illustrates a graftless spinal anterior fusion device 10. The device 10 includes a main body 12, which in this embodiment is substantially rectangularly shaped. However, one of ordinary skill will recognize that the main body 12 may be configured in shapes other than rectangular. The main body 12 also includes first and second opposite surfaces 14, 16 respectively. In this embodiment the first and second surfaces 14, 16 are substantially parallel, and include protruding members 18–21. The main body and protruding members are preferably a one piece (i.e., unitary) structure. The device 10 may also have a gentle curve/taper.

Figure 2:
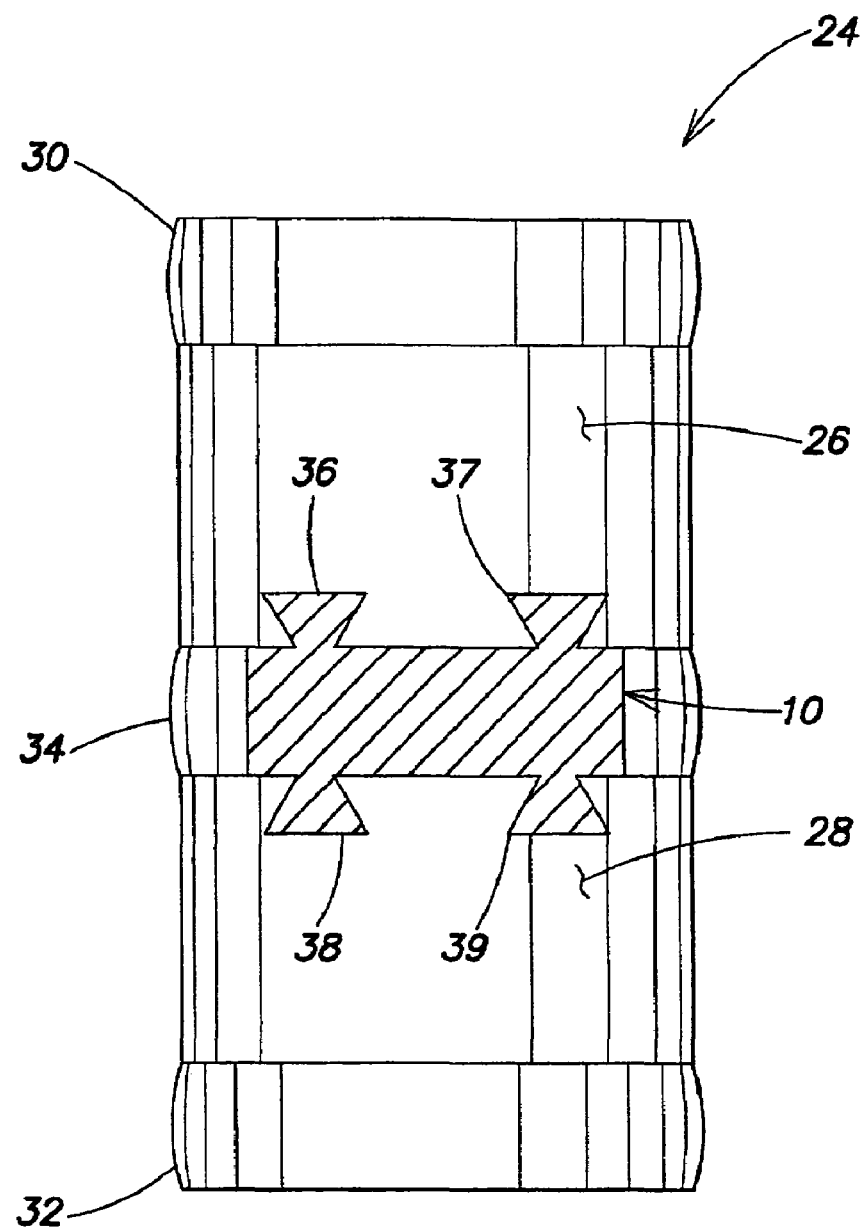
FIG. 2 illustrates a front view of the graftless spinal implant operably implanted within a spine.

FIG. 2 is a simplified illustration of the graftless spinal anterior fusion device 10 operably implanted within a spine 24. The spine includes vertebrae 26, 28 and natural disks 30, 32. The spine 24 also includes a diseased/damaged disk 34 that has been partially removed and replaced with the graftless spinal anterior fusion device 10 of the present invention. In preparation for the surgical insertion of the graftless spinal anterior fusion device 10, keyways 36–39 sized to securely accept an associated protruding member (e.g., 18–21) are formed in each of the vertebrae 26, 28 located adjacent to the damaged/diseased disk.

Figure 3:
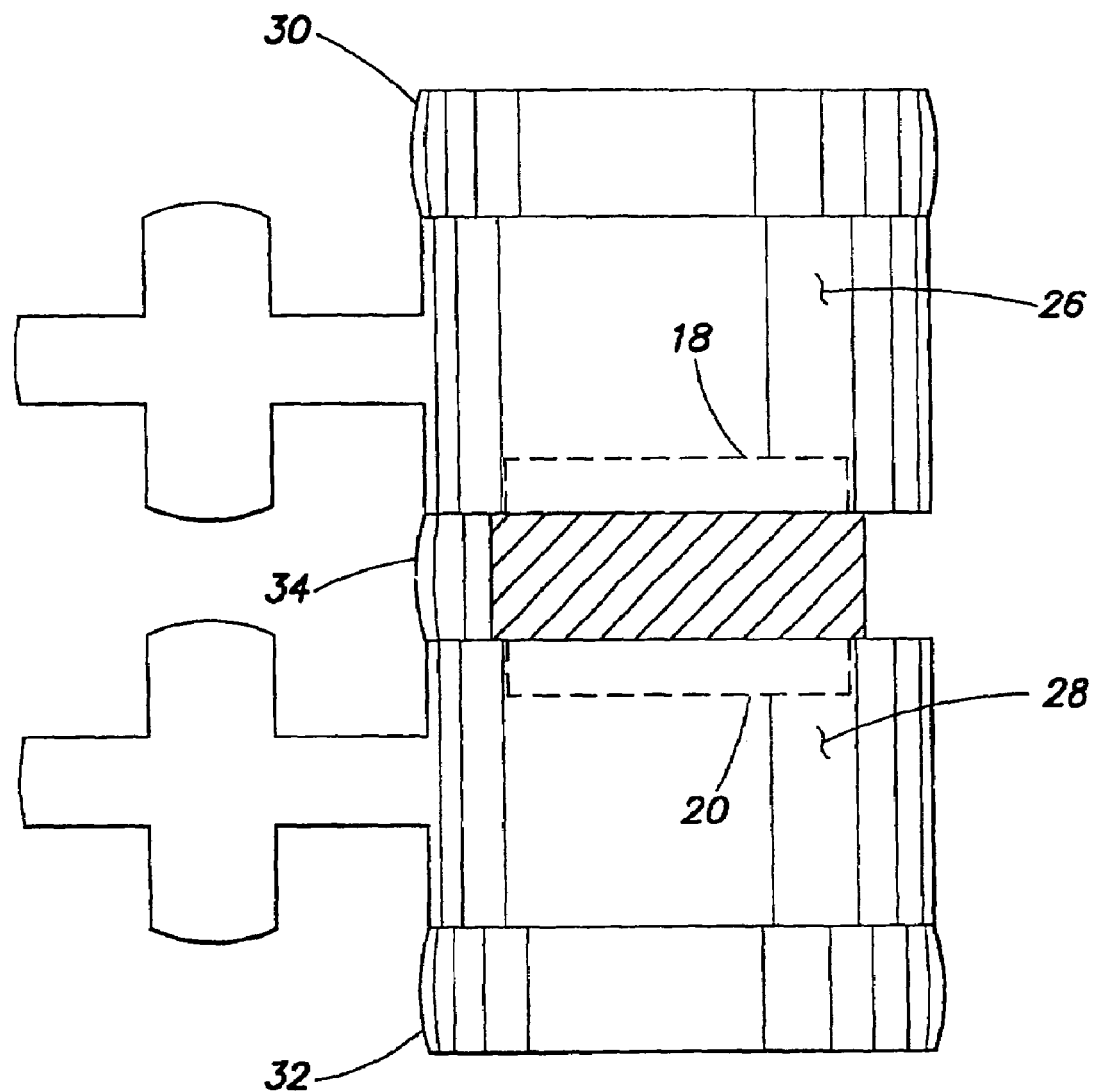
FIG. 3 illustrates a side view of the graftless spinal implant shown in FIG. 2.

FIG. 3 illustrates a side view of the graftless spinal implant 10 shown in FIG. 2. Notably, extension and rotational forces are neutralized by the protruding members.

According to an aspect of the present invention, the device 10 is coated with a bioactive coating, such as for example, hydroxyapatite, bioglass, biocomposites, hydroxypatite tricalcium phosphate, bone morphogenic protein, or other bone producing proteins. Significantly, the bioactive coating facilitates ongrowth/ingrowth of vertebral bone.

Figure 4:
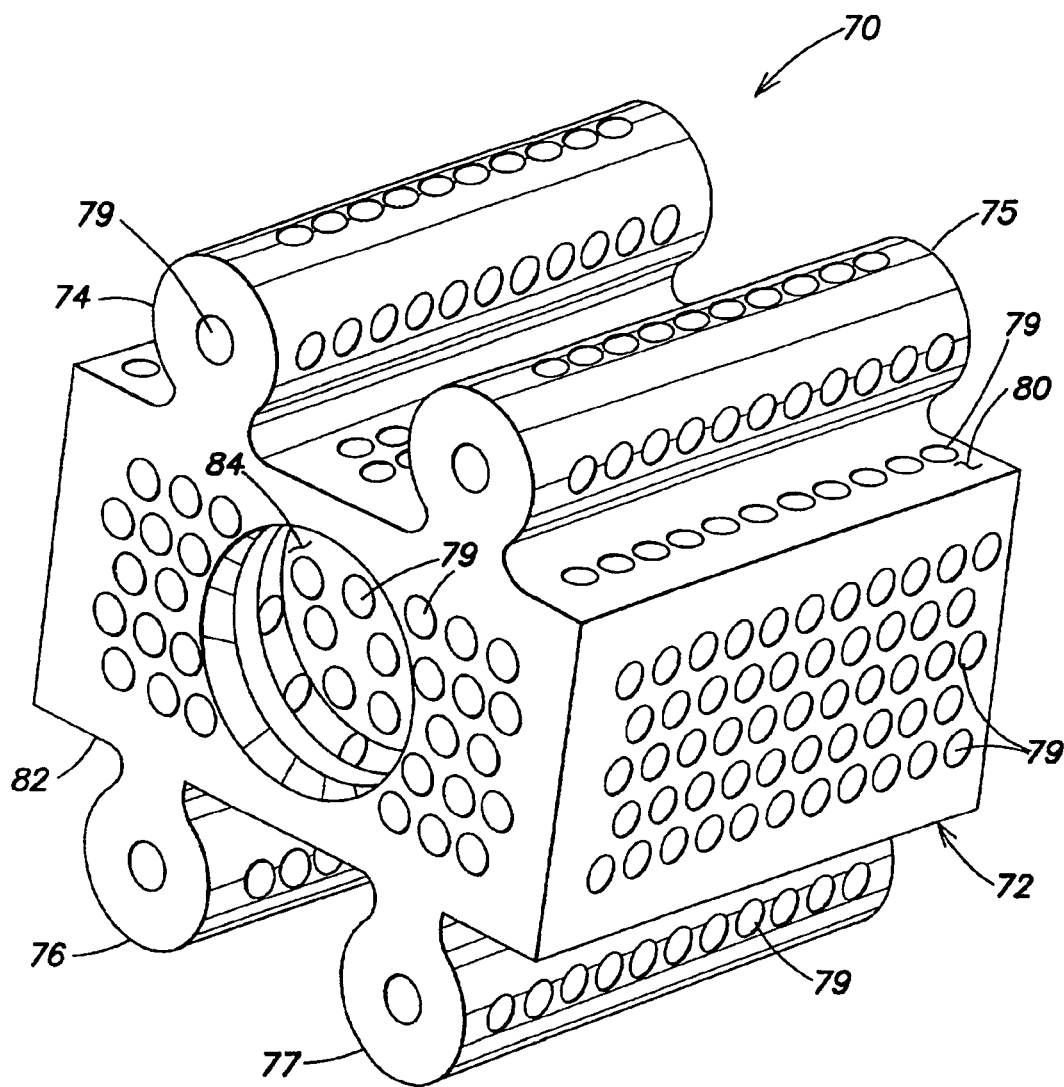
FIG. 4 illustrates a perspective view of a second embodiment of a graftless spinal implant.

FIG. 4 illustrates a perspective view of a second embodiment of a graftless spinal implant 70. This embodiment also includes a substantially rectangular main body 72, and at least one protrusion (e.g., 74–77) extending from each of first and second opposite surfaces 80, 82. Notably, the protrusions 74–77 are substantially cylindrically shaped. Of course, keyways (not shown) formed in adjacent vertebrae are shaped to accept the protrusions 74–77. In addition, the exterior surfaces of this graftless spinal implant 70 are textured/roughed and include a plurality of depressions 79, which increases the surface area of the implant. That is, the exterior surfaces of the graftless spinal implant 70 preferably include a plurality of shallow depressions 79 to facilitate fusion of the implant and adjacent bone. The textured surface may include beads, arc deposits, and/or synthetic foams. The exterior surfaces of the implant 70 are coated with a bioactive coating, such as for example, hydroxyapatite. This coating facilitates ongrowth/ingrowth of vertebral bone. The exterior surfaces of the device illustrated in FIGS. 1–4 in a preferred embodiment are preferably similarly roughened and include a plurality of depressions.

In an alternative embodiment, the implant 70 may include an opening 84 into which bone growth agents may be placed, as disclosed in the above identified U.S. patents incorporated herein by reference. The resultant device may no longer be considered a pure graftless device due to the inclusion of bone graft materials that are placed into the opening. Significantly, this device combines advantages of the graftless device discussed above, and features of the prior art graft techniques. The opening 84 may extend through the main body 72 (i.e., it is a through hole), or it may extend only partially through the main body 72. The surfaces that define the opening preferably may also be textured/ roughened and include shallow depressions/holes.

Figure 5:
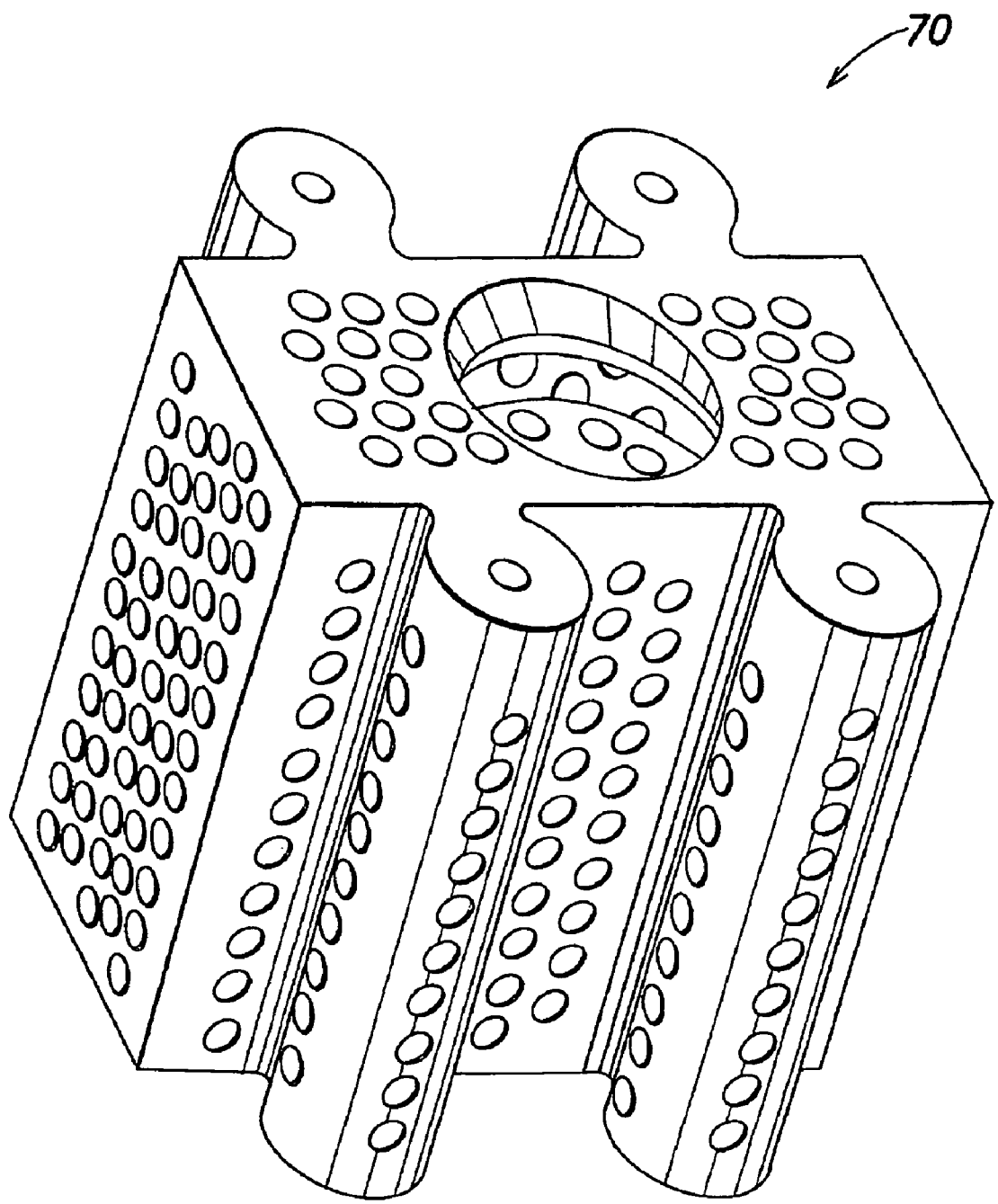
FIGS. 5–6 illustrate additional perspective views of the graftless spinal implant illustrated in FIG. 4.
Figure 6:
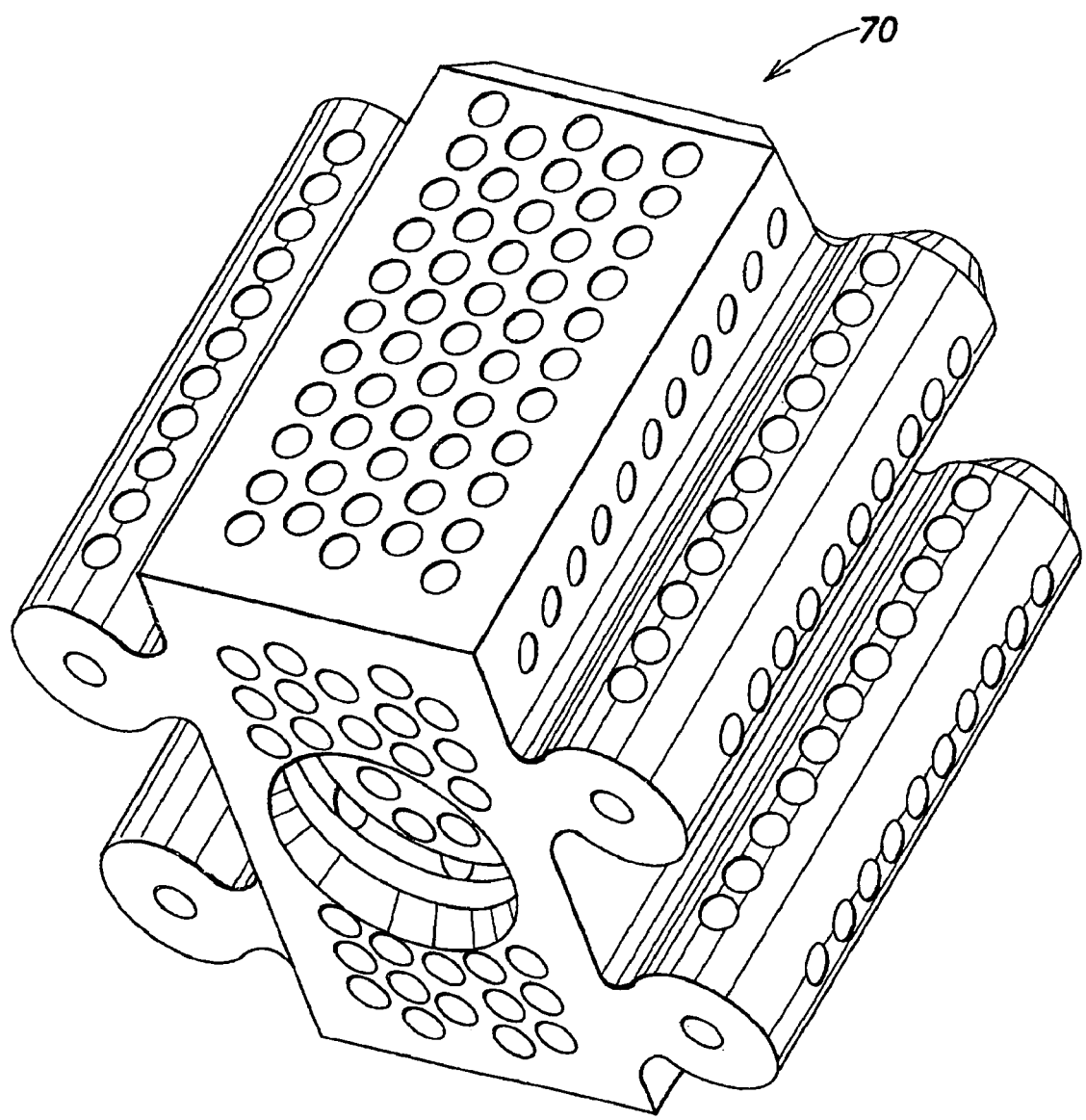

FIGS. 5 and 6 are additional perspective views of the graftless spinal implant 70.

Figure 7:
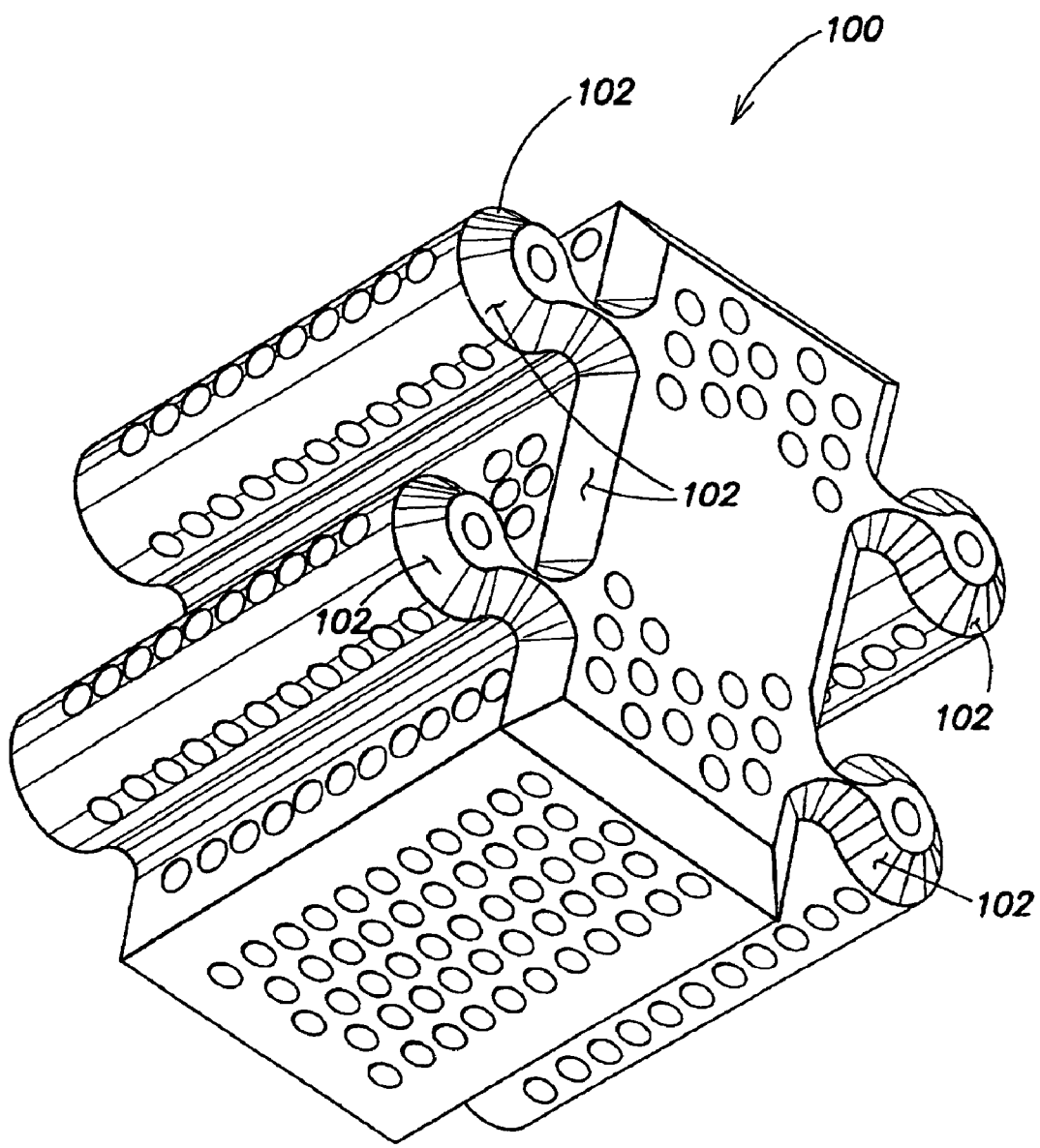
FIG. 7 illustrates yet another embodiment of a graftless spinal implant.

FIG. 7 illustrates a perspective view of yet another embodiment of a graftless spinal implant 100. This spinal implant is substantially the same as the implant illustrated in FIGS. 4–6, with the exception that this embodiment includes tapered edges 102 on at least one side of the device. The tapered edges 102 facilitate inserting the implant into the keyways (not shown) cut into the vertebrae. In this embodiment the implant 100 is also coated with a bioactive coating, such as for example, hydroxyapatite.

The implant itself may include a variety of presently acceptable biocompatible materials such as Titanium, Polyphenolsulfone, Polyaryletherketone (PEEK), Polysulfone, Acetal (Delrin), UHMW Polyethylene, and composites of these materials involving high strength carbon fibers or REM glass filaments to add tensile and shear strength. The implant may also be fabricated from human bone allograft material, autograft material, or bone substitute material, such as coral or calcium phosphate. The body of the implant may optionally have a modest taper.

Although the embodiments illustrated above employ protruding members that are substantially dovetail shaped or cylindrical/horse-shoe shaped, it is contemplated that essentially any shaped protruding member may be used with the bioactive coated implant of the present invention.

Although the present invention has been shown and described with respect to several preferred embodiments thereof, various changes, omissions and additions to the form and detail thereof, may be made therein, without departing from the spirit and scope of the invention.

What is claimed is:

1. A method for fusing a first vertebra to a second adjacent vertebra, the method comprising:
   a) providing an implant, the implant comprising a body having first and second opposite surfaces, wherein each of the surfaces includes at least one protruding member for securing the body to an adjacent vertebra, each protruding member of the implant characterized by a member longitudinal axis, each member having a profile perpendicular to the member's longitudinal axis that includes a generally arcuate portion that encompasses more than one hundred and eighty degrees of curvature as measured from the center of curvature, and each of the surfaces and protruding members including a bioactive coating;
   b) forming at least one keyway in the first vertebra corresponding to each of the at least one protruding members on the first surface, and at least one keyway in the second vertebra corresponding to each of the at least one protruding members on the second surface, wherein each keyway is characterized by a keyway longitudinal axis and has a profile perpendicular to the keyway's longitudinal axis including a generally arcuate portion that encompasses more than one hundred and eighty degrees of curvature as measured from the center of curvature,; and
   c) inserting the implant between the first vertebra and the second vertebra in a manner so that each protruding member slides into the corresponding keyway;

such that movement between the implant and the first vertebra along any perpendicular to the longitudinal axis of the at least one keyway in the first vertebra is prevented.

2. A method according to claim 1, wherein at least one of the opposite surfaces of the implant includes a plurality of protruding members.

\* \* \* \* \*